(12) United States Patent
Li et al.

(10) Patent No.: US 7,807,964 B2
(45) Date of Patent: Oct. 5, 2010

(54) ION MOBILITY SPECTROMETER AND METHOD THEREOF

(75) Inventors: Yuanjing Li, Beijing (CN); Zhiqiang Chen, Beijing (CN); Qingjun Zhang, Beijing (CN); Hua Peng, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 94 days.

(21) Appl. No.: 12/342,517

(22) Filed: Dec. 23, 2008

(65) Prior Publication Data

US 2009/0166530 A1 Jul. 2, 2009

(30) Foreign Application Priority Data

Dec. 27, 2007 (CN) .................. 2007 1 0304330

(51) Int. Cl.
*H01J 49/00* (2006.01)
*B01D 59/44* (2006.01)

(52) U.S. Cl. .............. 250/287; 250/286; 250/281; 250/283; 250/396 R; 250/423 R

(58) Field of Classification Search ............ 250/286, 250/287, 281, 283, 396 R, 423 R
See application file for complete search history.

(56) References Cited

U.S. PATENT DOCUMENTS

| | | | |
|---|---|---|---|
| 5,200,614 A | 4/1993 | Jenkins | 250/286 |
| 6,124,592 A * | 9/2000 | Spangler | 250/287 |
| 7,196,324 B2 * | 3/2007 | Verentchikov | 250/287 |
| 2010/0102219 A1 * | 4/2010 | Peng et al. | 250/283 |

FOREIGN PATENT DOCUMENTS

CN 200310106393.6 11/2003

* cited by examiner

*Primary Examiner*—Nikita Wells
(74) *Attorney, Agent, or Firm*—Westman, Champlin & Kelly, P.A.

(57) ABSTRACT

An ion mobility spectrometer and method thereof are disclosed. The ion mobility spectrometer comprises an electrode and an ion source arranged adjacent to the electrode, wherein the ion mobility spectrometer further comprises: a single or a group of focusing guide electrodes arranged on the side of the ion source far away from the electrode and shaped as a funnel to output ions from the ion source; and a storage section arranged on the ion-outputting side of the focusing guide electrode for storing ions generated from the ion source. With the scheme of separating the ion source and the storage region, the present invention can facilitate exchange of different ion sources, so that a source can be replaced with another different source without any change in the subsequent configuration. The storage section can be made very thin in the direction of ion movement, its diameter can be very large, and the internal electric field is almost zero. Thus, it is possible to collect a huge amount of ions with a very small cluster thickness and a directional velocity of almost zero, leading to reduction in spread of ion mobility spectrum and increase in resolution.

12 Claims, 2 Drawing Sheets

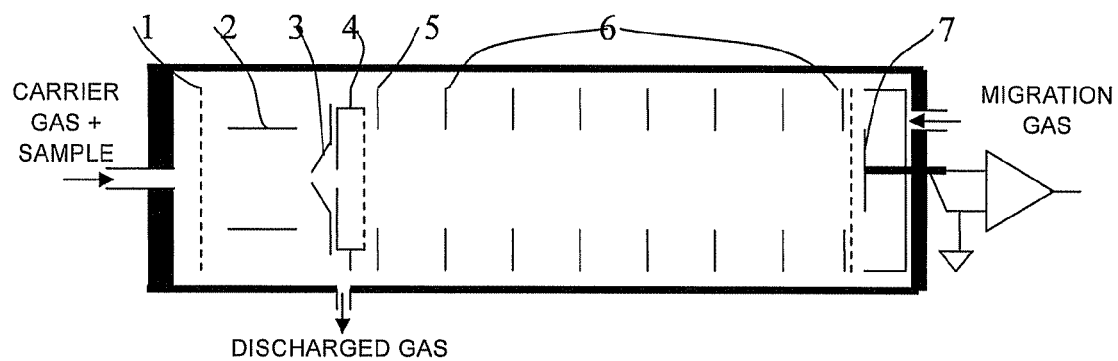
Fig. 1
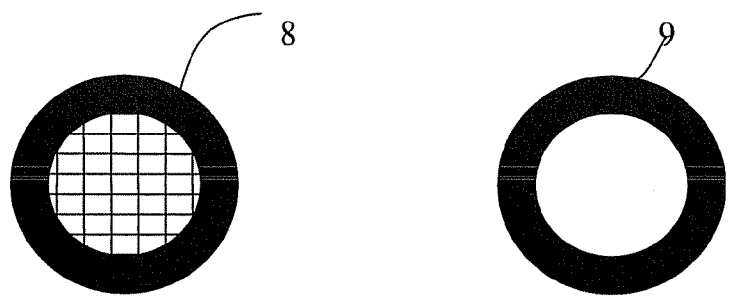
Fig. 2
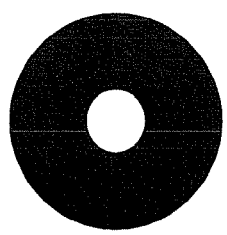 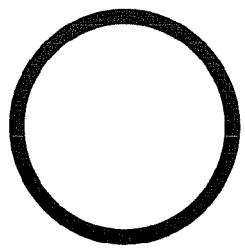 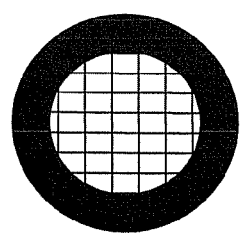
Fig. 3A    Fig. 3B    Fig. 3C
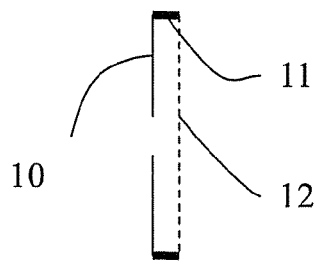
Fig. 4

ION MOBILITY SPECTROMETER AND METHOD THEREOF

The present application claims priority of Chinese patent application Ser. No. 200710304330.X, filed Dec. 27, 2007, the content of which is hereby incorporated by reference in its entirety.

BACKGROUND OF THE INVENTION

1. Field of Invention

The present invention relates to the field of safety inspection technology, in particular to an ion mobility spectrometer for inspecting drugs and explosives by means of ion mobility technique as well as an ion storage and extraction method applied to the ion mobility spectrometer.

2. Description of Prior Art

Ion mobility spectrometer discriminates different ions according to the fact that different ions have different drift velocities in a uniform weak electric field. The ion mobility spectrometer is usually formed of a sample input section, an ionization section, an ion gate, a drift region, a collection zone, a sensing circuit, a data acquisition and processing and control section, etc. In the prior art, Bradbury and Nielson gate is used to provide ions generated during the gate-opening phase to the drift region. Those ions generated during the gate-closing phase are scattered onto the tube wall by the ion gate and thus wasted without being stored.

CN Patent No. 200310106393.6 discloses an ion storage method, in which three pieces of mesh electrodes takes place of Bradbury and Nielson gate to form a storage region, and ions are stored in a non-electric field zone between the first two pieces of electrodes during the ion storage phase. When the ions are to be driven into the drift region for ion migration, the first piece of mesh electrode is changed to drive the ions into the space between the second and third pieces of mesh electrodes. Then, the second piece of mesh electrode is changed to drive the ions into the drift region for further migration and discrimination. Here, the stored ions have to pass through the mesh electrodes twice, and thus bumping and scattering will affect sensitivity. In additional, this process requires very complex control.

U.S. Pat. No. 5,200,614 also describes an ion storage method, in which sensitivity will be affected due to the problem of compounding between positive and negative ions at the ion storage phase. In this method, although the configuration is simplified by integrating the ionization zone and the storage region, some constraint is posed on the size and shape of the ion source, causing trouble in further application.

Both of the above solutions require a long gate-opening period to provide the ions into the drift region. This will cause spread in mobility spectrum peak shape and affect resolution for the same drift region.

SUMMARY OF THE INVENTION

An object of the present invention is to provide an ion mobility spectrometer and method thereof, with which sensitivity and resolution can efficiently improved plus simple and easy control.

In one aspect of the present invention, an ion mobility spectrometer is provided comprising an electrode and an ion source arranged adjacent to the electrode, wherein the ion mobility spectrometer further comprises: a focusing guide electrode arranged on the side of the ion source far away from the electrode and shaped as a funnel to output ions from the ion source; and a storage section arranged on the ion-outputting side of the focusing guide electrode for storing ions generated from the ion source.

Preferably, the storage section comprises a first end electrode, an intermediate electrode and a second end electrode arranged in this order.

Preferably, the first end electrode is formed of a metal sheet having a hole.

Preferably, the second end electrode is formed of a mesh-like metal sheet.

Preferably, the distance between the first and second end electrodes is less than 4 mm.

Preferably, the ion mobility spectrometer further comprises a further electrode arranged on the output side of the storage section.

Preferably, the distance between the storage section and the further electrode is less than 3 mm.

Preferably, voltage differences exist among the electrode, the shield metal case of the ion source, the focusing guide electrode and the storage section and are fixed relative to the voltages, and the further electrode is applied with a fixed voltage, so as to store ions in the storage section.

Preferably, the voltages on the first electrode, the shield metal case of the ion source, the focusing guide electrode and the storage section are changed to educe ions stored in the storage section.

Preferably, the ion source is isotope source, corona discharge, laser, ultraviolet or X-ray.

Preferably, each of the electrode and the further electrode is formed in a ring or mesh shape.

In another aspect of the present invention, a method for an ion mobility spectrometer is provided, the ion mobility spectrometer comprises an electrode and an ion source arranged adjacent to the electrode, wherein the ion mobility spectrometer further comprises: a focusing guide electrode arranged on the side of the ion source far away from the electrode and shaped as a funnel to output ions from the ion source; a storage section arranged on the ion-outputting side of the focusing guide electrode for storing ions generated from the ion source; and a further electrode arranged on the output side of the storage section; the method comprises an ion storage step of applying voltages to the electrode, the shield metal case of the ion source, the focusing guide electrode and the storage section so that voltage differences exist among them and are fixed relative to the voltages, and applying a fixed voltage to the further electrode, so as to store ions in the storage section; an ion extraction step of changing the voltages on the electrode, the shield metal case of the ion source, the focusing guide electrode and the storage section to educe ions stored in the storage section.

With the scheme of separating the ion source and the storage region, the present invention can facilitate exchange of different ion sources, so that a source can be replaced with another different source without any change in the subsequent configuration.

The mesh electrode, the ion source, the focusing guide electrode and the storage section form a combined electrode. Voltage differences exist among the mesh electrode, the ion source, the focusing guide electrode and the storage section and are fixed relative to the voltages, and the first ring electrode is applied with a fixed voltage. As such, the voltage on the combined electrode can be floating and changing to enable storage and extraction of ions.

At the ion storage step, positive or negative ions to be collected are driven by the electric field and drift through the focusing guide electrode into the storage section for storing. The storage section can be made very thin in the direction of ion movement, its diameter can be very large, and the internal electric field is almost zero. Thus, it is possible to collect a huge amount of ions with a very small cluster thickness and a directional velocity of almost zero, leading to reduction in spread of ion mobility spectrum and increase in resolution.

At the ion extraction step, the voltage on the combined electrode is changed to push the ions into the drift region. Immediately following this, the overall voltage is restored to the storage state.

BRIEF DESCRIPTION OF THE DRAWINGS

FIG. 1 is a schematic diagram of the configuration of an ion mobility spectrometer according to an embodiment of the present invention;

FIG. 2 is a schematic diagram of an electrode used in the ion mobility spectrometer according to an embodiment of the present invention;

FIGS. 3A to 3C are schematic side views of a storage section in the ion mobility spectrometer according to an embodiment of the present invention;

FIG. 4 is a schematic front view of the storage section in the ion mobility spectrometer according to an embodiment of the present invention;

DETAILED DESCRIPTION OF PREFERRED EMBODIMENTS

Figure 5:
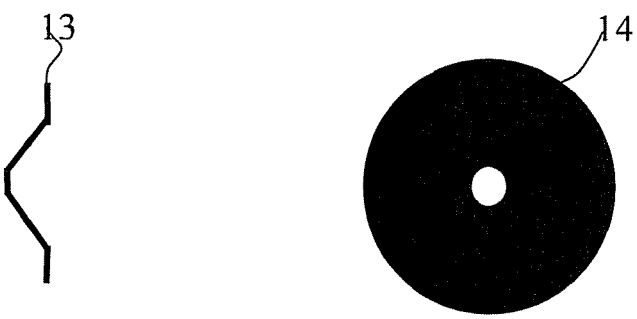
FIG. 5 shows schematic front and side views of a focusing guide electrode used in the ion mobility spectrometer according to an embodiment of the present invention.

Now, the present invention will be further illustrated with reference to the figures and embodiments. The present invention can be applied in either a negative ion mode or a positive ion mode. For the purpose of conciseness and illustration, only the positive ion mode is specifically described here.

FIG. 1 is a schematic diagram of the configuration of an ion mobility spectrometer according to an embodiment of the present invention. As shown in FIG. 1, the ion mobility spectrometer according to the present embodiment is provided with a mesh electrode 1, an ion source 2, a focusing guide electrode 3, a storage section 4, a first ring or mesh electrode 5, a further ring electrode 6 and a Faraday plate 7, etc.

According to the present embodiment, the ion source 2 can be an isotope source like $^{63}$Ni, or can be other source like corona discharge, laser, ultraviolet or X-ray.

As shown in FIG. 2, the mesh electrode 1 can be shaped as denoted by reference symbol 8, including various types of holes, such as hexagon or circular hole. The first ring electrode 5 can be shaped as denoted by reference symbol 9 or as a ring donated by reference symbol 8.

FIGS. 3A to 3C are schematic side views of a storage section in the ion mobility spectrometer according to the present embodiment. FIG. 4 is a schematic front view of the storage section in the ion mobility spectrometer according to the present embodiment.

As shown in FIG. 4, the storage section 4 is a metal case of which one side is formed of a thin metal sheet 10 having a small circular hole (see FIG. 3A), the intermediate part is formed of a circular ring 11 (see FIG. 3B), and the other side is formed of a thin metal sheet 12 shaped as a mesh (see FIG. 3C). The wires of the mesh are required to be as thin as possible. The distance between the two metal sheets 10 and 12 should be less than 4 mm. Also, a non-electric field zone is formed inside the storage section.

As shown in FIG. 5, reference symbols 13 and 14 denote the front and side views of the focusing guide electrode 3, respectively. The focusing guide electrode 3 is shaped as a funnel, which is getting bigger from the side adjacent to the ion source 2 to the other side far away from the ion source 2, to form a focusing electric field for guiding the ions. Also, a group of such electrodes can be used for focusing the ions. Further, the distance between the storage section 4 and the first ring electrode 5 should be less than 3 mm to facilitate push-out of the ions.

Figure 6:
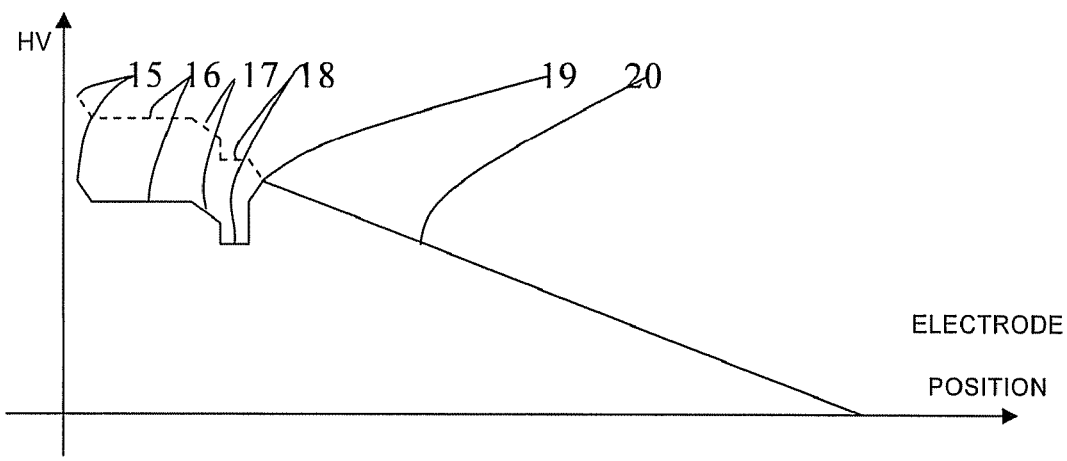
FIG. 6 is a schematic diagram showing the potentials of respective electrodes when the ion mobility spectrometer according to an embodiment of the present invention operates in a positive ion mode.

FIG. 6 is a schematic diagram showing the potentials of the respective electrodes when the ion mobility spectrometer according to the present embodiment operates in a positive ion mode. As shown in FIG. 6, reference symbols 15 represents the voltage applied to the mesh electrode 1, reference symbols 16 represents the voltage applied to the ion source 2, reference symbols 17 represents the voltage applied to the focusing guide electrode 3, reference symbols 18 represents the voltage applied to the storage section 4, and reference symbols 19 represents the voltage applied to the first ring or mesh electrode 5.

In FIG. 6, the solid line denotes the potentials at the mesh electrode 1, the ion source 2, the focusing guide electrode 3 and the storage section 4 in the ion storage state, and the dashed line denotes the potentials at the mesh electrode 1, the ion source 2, the focusing guide electrode 3 and the storage section 4 in the ion extraction state. The voltages applied to the mesh electrode 1, the ion source 2, the focusing guide electrode 3 and the storage section 4 can be floating. There are voltage differences between the mesh electrode 1 and the shield metal case of the ion source 2, also and the focusing guide electrode 3 and the storage section 4. The first ring or mesh electrode 5 is applied with a fixed voltage. The first ring or mesh electrode 5 and the subsequent ring electrode 6 are applied with a uniformly decreasing voltage to form the drift region. The solid line 20 represents voltages at points after the ring electrode, which voltages remain unchanged at both of the storage and ion extraction phases.

At the ion storage phase, positive ions will move to a potential well formed as denoted by reference symbol 18 to be stored. The voltages at the respective points can be adjusted to form a potential well of a suitable thickness under the requirement of maximal storage capacity and fast extraction.

At the ion extraction phase, the voltages applied to the mesh electrode 1, the ion source 2, the focusing guide electrode 3 and the storage section 4 are simultaneously raised to a voltage denoted by the dashed line, so that the ions are educed into the drift region for drifting and discrimination. Subsequently, the overall voltages are restored to those at the storage phase.

Figure 7:
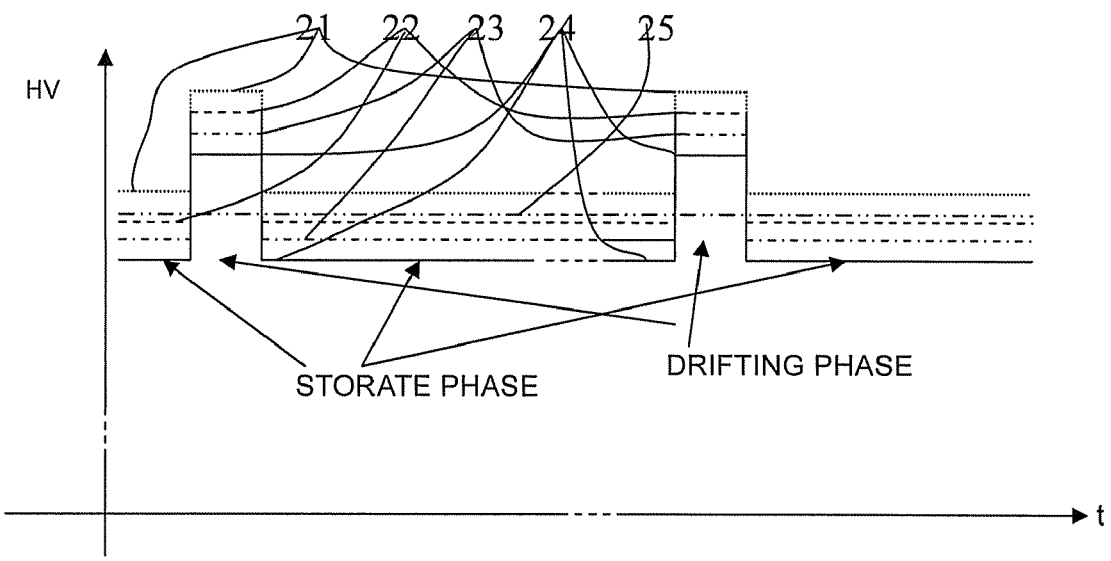
FIG. 7 is a schematic diagram showing voltage change vs. time of respective electrodes when the ion mobility spectrometer according to an embodiment of the present invention operates in a positive ion mode.

FIG. 7 is a schematic diagram showing voltage change vs. time of respective electrodes when the ion mobility spectrometer according to the present embodiment operates in a positive ion mode. As shown in FIG. 7, reference symbols 21, 22, 23, 24, 25 denote wave forms of the voltages applied to the mesh electrode 1, the ion source 2, the focusing guide electrode 3, the storage section 4 and the first ring electrode 5, with the voltages changing over time.

At the storage phase, the voltages on the mesh electrode 1, the ion source 2, the focusing guide electrode 3 are each higher than that on the storage section 4, and the voltage 25 on the first ring or mesh electrode 5 is also higher than the voltage 22 on the storage section 4. By adjusting the baseline voltages denoted by reference symbols 21, 22, 23, 24, 25 and the jump magnitude, the ion storage capacity can be maximized, and the ions can be pushed out rapidly.

When the ions are to be driven from the storage section to the drift region, the voltages applied to the mesh electrode 1, the ion source 2, the focusing guide electrode 3, the storage section 4 are simultaneously raised by certain magnitude to be higher than the voltage 25 on the first ring electrode 5. In this way, the ions can be driven into the drift region. After that, the voltages are restored to those in the storage state.

As mentioned above, with the scheme of separating the ion source and the storage region, the present invention can facilitate exchange of different ion sources, so that a source can be replaced with another different source without any change in the subsequent configuration.

The mesh electrode 1, the ion source 2, the focusing guide electrode 3 and the storage section 4 form a combined electrode. Voltage differences exist among the mesh electrode 1, the shield metal case of the ion source 2, the focusing guide electrode 3 and the storage section 4 and are fixed relative to the voltages, and the first ring electrode 5 is applied with a fixed voltage. As such, the voltage on the combined electrode can be floating and changing to enable storage and extraction of ions.

At the ion storage phase, positive or negative ions to be collected are driven by the electric field and drift through the focusing guide electrode 3 into the storage section 4 for storing. The storage section 4 can be made very thin in the direction of ion movement, its diameter can be very large, and the internal electric field is almost zero. Thus, it is possible to collect a huge amount of ions with a very small cluster thickness and a directional velocity of almost zero, leading to reduction in spread of ion mobility spectrum and increase in resolution.

At the ion extraction phase, the voltage on the combined electrode is changed to push the ions into the drift region. Immediately following this, the overall voltage is restored to the storage state.

The foregoing description is only the preferred embodiments of the present invention and not intended to limit the present invention. Those ordinarily skilled in the art will appreciate that any modification or substitution in the principle of the present invention shall fall into the scope of the present invention defined by the appended claims.

What is claimed is:

1. An ion mobility spectrometer comprising:
an electrode; and
an ion source arranged adjacent to the electrode;
wherein the ion mobility spectrometer further comprises:
a focusing guide electrode arranged on the side of the ion source far away from the electrode and shaped as a funnel to output ions from the ion source; and
a storage section arranged on the ion-outputting side of the focusing guide electrode for storing ions generated from the ion source.

2. The ion mobility spectrometer of claim 1, wherein the storage section comprises a first end electrode, an intermediate electrode and a second end electrode arranged in this order.

3. The ion mobility spectrometer of claim 2, wherein the first end electrode formed of a metal sheet having a hole.

4. The ion mobility spectrometer of claim 2, wherein the second end electrode is formed of a mesh-like metal sheet.

5. The ion mobility spectrometer of claim 2, wherein the distance between the first and second end electrodes is less than 4 mm.

6. The ion mobility spectrometer of claim 1, wherein the ion mobility spectrometer further comprises a further electrode arranged on the output side of the storage section.

7. The ion mobility spectrometer of claim 6, wherein the distance between the storage section and the further electrode is less than 3 mm.

8. The mobility of claim 6, wherein voltage differences exist among the electrode, the shield metal case of the ion source, the focusing guide electrode and the storage section and are fixed relative to the voltages, and the further electrode is applied with a fixed voltage, so as to store ions in the storage section.

9. The ion mobility spectrometer of claim 8, wherein the voltages on the first electrode, the shield metal case of the ion source, the focusing guide electrode and the storage section are changed to educe ions stored in the storage section.

10. The ion mobility spectrometer of claim 1, wherein the ion source is isotope source, corona discharge, laser, ultraviolet or X-ray.

11. The ion mobility spectrometer of claim 6, wherein each of the electrode and the further electrode is formed in a ring or mesh shape.

12. A method for an ion mobility spectrometer comprising an electrode and an ion source arranged adjacent to the electrode, wherein the ion mobility spectrometer further comprises:
a focusing guide electrode arranged on the side of the ion source far away from the electrode and shaped as a funnel to output ions from the ion source;
a storage section arranged on the ion-outputting side of the focusing guide electrode for storing ions generated from the ion source; and
a further electrode arranged on the output side of the storage section; the method comprises:
an ion storage step of applying voltages to the electrode, the shield metal case of the ion source, the focusing guide electrode and the storage section so that voltage differences exist among them and are fixed relative to the voltages, and applying a fixed voltage to the further electrode, so as to store ions in the storage section;
an ion extraction step of changing the voltages on the electrode, the shield metal case of the ion source, the focusing guide electrode and the storage section to educe ions stored in the storage section.

* * * * *